United States Patent
Ting-Jenulis et al.

(10) Patent No.: US 8,491,921 B2
(45) Date of Patent: Jul. 23, 2013

(54) COMPOSITIONS AND METHODS FOR TINTING KERATIN MATERIAL

(75) Inventors: Arlene G. Ting-Jenulis, Smithtown, NY (US); John R. Castro, Hauppauge, NY (US)

(73) Assignee: ELC Management, LLC, New York, NY (US)

( * ) Notice: Subject to any disclaimer, the term of this patent is extended or adjusted under 35 U.S.C. 154(b) by 9 days.

(21) Appl. No.: 13/366,794

(22) Filed: Feb. 6, 2012

(65) Prior Publication Data

US 2013/0045254 A1 Feb. 21, 2013

Related U.S. Application Data

(60) Provisional application No. 61/524,349, filed on Aug. 17, 2011.

(51) Int. Cl.
*A61Q 1/02* (2006.01)
*A61Q 1/10* (2006.01)

(52) U.S. Cl.
USPC .......................................... 424/401; 424/70.7

(58) Field of Classification Search
None
See application file for complete search history.

(56) References Cited

U.S. PATENT DOCUMENTS

| | | |
|---|---|---|
| 3,439,088 A | 4/1969 | Edman et al. |
| 3,818,105 A | 6/1974 | Coopersmith et al. |
| 5,389,363 A | 2/1995 | Snyder et al. |
| 5,993,834 A | 11/1999 | Shah et al. |
| 6,458,390 B1 | 10/2002 | Manelski et al. |
| 6,908,621 B2 | 6/2005 | Jose et al. |
| 6,967,024 B2 | 11/2005 | Scancarella et al. |
| 7,005,134 B2 | 2/2006 | Brieva et al. |
| 2003/0082125 A1 | 5/2003 | Grimm |
| 2007/0041928 A1 | 2/2007 | Chen et al. |

FOREIGN PATENT DOCUMENTS

| | | |
|---|---|---|
| WO | 2005-060922 A1 | 7/2005 |
| WO | 2007-013943 A2 | 2/2007 |
| WO | 2010-105952 A2 | 9/2010 |

OTHER PUBLICATIONS

Lash Tint; Mintel GNPD; Record ID: 10116111; Revlon; Revlon ColorStay Overtime; Colour Cosmetics; Eye Colour Cosmetics—Eye Lash; Canada; Aug. 2002.

*Primary Examiner* — Jyothsna Venkat
(74) *Attorney, Agent, or Firm* — Julie M. Blackburn

(57) ABSTRACT

A cosmetic composition comprising at least one volatile solvent, at least one crosslinked silicone film former, at least one silicone gum, and at least one pigment composition present in an amount sufficient to provide the cosmetic composition with a pigment contrast ratio of greater than 35 and a method for maximizing the intensity and opacity of a color cosmetic composition.

9 Claims, No Drawings

COMPOSITIONS AND METHODS FOR TINTING KERATIN MATERIAL

This application claims priority from U.S. Provisional Patent Application Ser. No. 61/524,349, filed Aug. 17, 2011 and Australian Patent Application No. 2011213717, filed Aug. 17, 2011.

TECHNICAL FIELD

The invention is in the field of compositions for application to keratinous material to provide long lasting color.

BACKGROUND OF THE INVENTION

Women who have light brown, blonde, or gray hair often desire eyebrows and eyelashes that are darker in color. They have a number of options including dyeing lashes and brows with permanent hair color or using products that apply temporary color such as mascara and brow products. The latter exhibits wear that typically lasts from 4 to 12 hours. While such products are generally effective, they do exhibit drawbacks such as smudging or wearing away with water, tears, or perspiration. In addition, the pigments typically used often provide a more matte color rather than the high color intensity desired by consumers. Consumers especially desire high intensity black or black/brown in their lash color. This is often difficult to achieve with currently available cosmetic pigments. For example, carbon black is well known to provide high intensity color. However, it is difficult to formulate with carbon black in its native state because the particles are very small and typically exhibit polarity and a somewhat sheer color that doesn't provide maximum color intensity. While it is known to treat carbon black pigments to enhance their formulation efficacy, in some cases the treatment provides particles that are even more sheer.

Accordingly, there is a need for pigmented compositions to color keratinous materials such as eyelashes or eyebrows that have longer lasting color and reduced smudging and wear away, preferably wear that lasts from one to three days. In addition, there is a need to have such color compositions exhibit an intensity of color that satisfies consumers and also provides some longevity.

SUMMARY OF THE INVENTION

The invention is directed to a cosmetic composition comprising at least one volatile solvent, at least one crosslinked silicone film former, at least one silicone gum, and at least one pigment composition wherein the cosmetic composition containing the pigment composition has a pigment contrast ratio of greater than 35.

DETAILED DESCRIPTION

All percentages mentioned herein are percentages by weight unless otherwise indicated.

All documents mentioned herein are incorporated by reference in their entirety.

The term "oil" means a pourable liquid at room temperature, e.g. 25° C.

Volatile Solvents

Suitable volatile solvents generally have a viscosity ranging from about 0.5 to 5 centistokes (cst) at 25° C. and include linear silicones, cyclic silicones, branched silicones, paraffinic hydrocarbons, or mixtures thereof. The volatile solvent may be present in amounts ranging from about 0.1 to 95%, preferably 0.5 to 85%, more preferably from about 1 to 80%.

Cyclic silicones are one type of volatile silicone that may be used in the composition. Such silicones have the general formula:

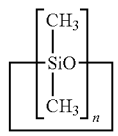

where n=3-6, preferably 4, 5, or 6.

Also suitable are linear volatile silicones, for example, those having the general formula:

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the trade names Dow Corning 244, 245, 344, and 200 fluids. These fluids include hexamethyldisiloxane (viscosity 0.65 cst), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

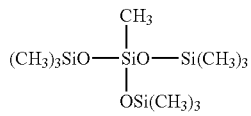

Methyl trimethicone may be purchased from Shin-Etsu Silicones under the tradename TMF-1.5, having a viscosity of 1.5 centistokes at 25° C.

Also suitable as the volatile solvents are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference.

Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

The Crosslinked Silicone Film Former

The composition comprises at least one crosslinked silicone film former. The crosslinked silicone film former may be present in amounts ranging from about 0.1 to 85%, preferably from about 0.5 to 80%, more preferably from about 1 to 75%.

Suitable crosslinked silicone film formers including crosslinked linear or branched silicones such as those having M, or monofunctional units; in combination with one or more of D, or difunctional units; T, or trifunctional units; or Q, or quadrifunctional units.

The term "M" means "monofunctional" and refers to a siloxy unit that contains one silicon atom bonded to one oxygen atom, with the remaining three substituents on the silicon atom being other than oxygen. In particular, in a monofunctional siloxy unit, the oxygen atom present is shared by 2 silicon atoms when the monofunctional unit is polymerized with one or more of the other units. In standard silicone nomenclature the monofunctional siloxy unit is designated by the letter "M" and means a unit having the general formula:

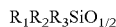

wherein $R_1$, $R_2$, and $R_3$ are each independently $C_{1-30}$, preferably $C_{1-10}$, more preferably $C_{1-4}$ straight or branched chain alkyl, which may be substituted with phenyl or one or more hydroxyl groups; phenyl; alkoxy (preferably $C_{1-22}$, more preferably $C_{1-6}$); hydroxyl; or hydrogen. The $SiO_{1/2}$ designation means that the oxygen atom in the monofunctional unit is bonded to, or shared, with another silicon atom when the monofunctional unit is polymerized with one or more of the other types of units. For example, when $R_1$, $R_2$, and $R_3$ are methyl the resulting monofunctional unit is of the formula:

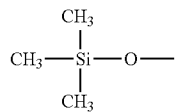

When this monofunctional unit is polymerized with one or more of the other units the oxygen atom will be shared by another silicon atom, that is, the silicon atom in the monofunctional unit is bonded to ½ of this oxygen atom.

The term "D" in standard silicone nomenclature means "difunctional" with respect to a siloxy unit. If the D unit is substituted with substituents other than methyl the "D'" ("D prime") designation is sometimes used, which indicates substituents other than methyl. For purposes of this disclosure, a "D" unit has the general formula:

wherein $R_1$ and $R_2$ are defined as above. The $SiO_{2/2}$ designation means that the silicon atom in the difunctional unit is bonded to two oxygen atoms when the unit is polymerized with one or more of the other units. For example, when $R_1$, $R_2$, are methyl the resulting difunctional unit is of the formula:

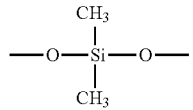

When this difunctional unit is polymerized with one or more of the other units the silicon atom will be bonded to two oxygen atoms, or in other words, will share two one-halves of an oxygen atom.

The term "T" in silicone nomenclature means "trifunctional" and refers to a trifunctional siloxy unit. A "T" unit has the general formula: $R_1SiO_{3/2}$ wherein $R_1$ is as defined above. The $SiO_{3/2}$ designation means that the silicon atom is bonded to three oxygen atoms when the unit is copolymerized with one or more of the other units. For example when $R_1$ is methyl the resulting trifunctional unit is of the formula:

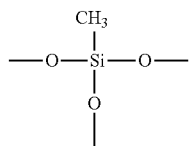

When this trifunctional unit is polymerized with one or more of the other units, the silicon atom shares three oxygen atoms with other silicon atoms, or in other words will share three halves of an oxygen atom.

The term "Q" means "tetrafunctional" with respect to a siloxy unit. A "Q" unit has the general formula:

The $SiO_{4/2}$ designation means that the silicon shares four oxygen atoms, that is, four halves, with other silicon atoms when the tetrafunctional unit is polymerized with one or more of the other units. The $SiO_{4/2}$ unit is best depicted as follows:

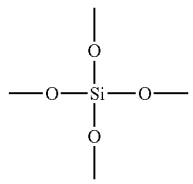

The crosslinked silicones used in the composition of the invention may contain any combination of M, D, T, and Q units described above.

The crosslinked silicones used in the compositions of the invention are made according to processes well known in the art. In general siloxane polymers are obtained by hydrolysis of silane monomers, preferably chlorosilanes. The chlorosilanes are hydrolyzed to silanols and then condensed to form siloxanes. For example, Q units are often made by hydrolyzing tetrachlorosilanes in aqueous or aqueous/alcoholic media to form hydroxy substituted silanes which are then condensed or polymerized with other types of silanol substituted units. Because the hydrolysis and condensation may take place in aqueous or aqueous/alcoholic media wherein the alcohols are preferably lower alkanols such as ethanol, propanol, or isopropanol, the units may have residual hydroxyl or alkoxy functionality as depicted above. The silicones may be crosslinked with a number of different crosslinking agents including but not limited to silica silylate, alpha omega dienes, methylhydrogensiloxanes, and the like.

Preferably, the crosslinked silicones are made by hydrolysis and condensation in aqueous/alcoholic media, which provides resins that have residual silanol and alkoxy functionality. In the case where the alcohol is ethanol, the result is a resin that has residual hydroxy or ethoxy functionality on the siloxane polymer. The silicone film forming polymers used in the compositions of the invention are generally made in accordance with the methods set forth in Silicon Compounds (Silicones), Bruce B. Hardman, Arnold Torklelson, General Electric Company, Kirk-Othmer Encyclopedia of Chemical Technology, Volume 20, Third Edition, pages 922-962, 1982, which is hereby incorporated by reference in its entirety.

The crosslinked silicone film former may be a liquid, semi-solid, or solid at room temperature.

Examples of crosslinked silicone film formers that may be used in the composition of the invention include but are not limited to dimethicone silylate, trimethylsiloxysilicate, cetearyl dimethicone crosspolymer, cetearyl dimethicone/vinyl dimethicone crosspolymer, dilauroyltrimethylolpropane siloxysilicate, dimethicone crosspolymer-3, dimethicone silsesquioxane copolymer, dimethicone/vinyl dimethicone crosspolymer, dimethicone vinyltrimethylsiloxysilicate copolymer, diphenyldimethicone crosspolymer, divinyldimethicone/dimethicone crosspolymer, and so on. Particularly preferred is trimethylsiloxysilicate, dimethicone silylate, or a mixture of both.

The Silicone Gum

Also suitable for use as an oil phase structuring agent are one or more silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

The silicone gums that are used in the compositions include, but are not limited to, those of the general formula wherein:

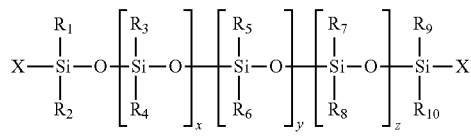

$R_1$ to $R_9$ are each independently an alkyl having 1 to 30 carbon atoms, aryl, or aralkyl; and X is OH or a $C_{1-30}$ alkyl, or vinyl; and wherein x, y, or z may be zero with the proviso that no more than two of x, y, or z are zero at any one time, and further that x, y, and z are such that the silicone gum has a viscosity of at least about 500,000 cst, ranging up to about 100 million centistokes at 25° C. Preferred is where R is methyl or OH.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

The Pigment

The composition of the invention contains a pigment composition that, when incorporated into the cosmetic composition, will provide a cosmetic composition that has a pigment contrast ratio of at least about 35, more preferably from about 35 to 80, most preferably from about 40 to 75. Without being bound by this explanation, it has been found that when the pigment contrast ratio is within these ranges the composition provides optimized color in terms of intensity and opacity. For example, color cosmetic compositions where the color is opaque provide excellent coverage but color intensity is often reduced. On the other hand, cosmetic compositions that provide high color intensity often do so at the expense of opacity. If both opacity and intensity are carefully controlled the resulting composition will have an opacity and color intensity that is maximized in both respects.

The pigment composition may be present in amounts ranging from about 0.1 to 80%, preferably from about 0.5 to 75%, more preferably from about 1 to 70%.

The term "pigment composition" when used herein shall mean the total of all pigments, including organic and inorganic pigments present in the cosmetic composition but excludes titanium dioxide and non-pigmented particulate materials that are otherwise known as fillers.

The organic pigments may be aromatic types including azo, indigoid, triphenylmethane, anthroquinone, and xanthine dyes which are designated as D&C and FD&C blue, brown, green, orange, red, yellow, violet and so on. The organic pigments may also be in the form of water soluble or insoluble metallic salts of certified color additives, referred to as the Lakes.

Inorganic pigments include iron oxides, ultramarines, chromium, chromium hydroxide colors, carbon black, and mixtures thereof The pigments may be present in the solid particulate or liquid form. If particulates, particle sizes range from about 0.01 to 200 microns, preferably from about 0.01 to 100 microns, more preferably from about 0.01 to 50 microns.

In one preferred embodiment the pigment composition comprises carbon black in combination with one or more D&C or FD&C organic pigments selected from blue, green, black, violet or mixtures thereof.

In another preferred embodiment the pigment composition comprises carbon black in combination with one or more organic pigments which may include D&C or FD&C blue.

In yet another preferred embodiment the pigment composition comprises carbon black either alone or treated with one or more ingredients to form a pigment complex.

Particularly preferred is a pigment such as carbon black that is treated with at least one polyester or polyamide, such as disclosed in U.S. Pat. No. 5,993,834 to form a pigment complex. More specifically, the carbon black is treated with a water dispersible polyester or polyesteramide by grinding with the polyester or polyamide. The polyester or polyamide is made by reacting at least one difunctional carboxylic acid with at least one difunctional sulfomonomer which optionally may contain a metallic group, at least one difunctional reactant which may be a glycol, and a hydroxycarboxylic or aminocarboxylic acid. Examples of such polyesters or polyamides including, but are not limited to those sold by Eastman Chemical under the tradename AQ, such as AQ 55S. Others polyesters include those having the CTFA names Polyester-1 (copolymer of t-butylacrylamide, cyclohexane dimethanol, diethylene glycol, isophthalic acid, sodium isophthalic acid sulfonate and one or more monomers of acrylic acid, methacrylic acid or one of their simple esters); Polyester-2 (cyclohexanedicarboxylic acid, Adipic Acid, Trimethylolpropane and Hexanediol); Polyester-3 (glycol, terephthalic acid, isophthalic acid, cyclohexanedimethanol and norbornanediamine); Polyester-4 (copolymer formed by the condensation of Adipic Acid and Pentaerythritol endcapped with Caproic Acid, heptanoic acid, Caprylic Acid and Capric Acid); Polyester-5 (Diglycol/CHDM/Isophthalates/SIP Copolymer); Polyester-6 (condensation product of Polyhydroxystearic Acid, Polyglycerin-4, Sebacic Acid, and Isostearic Acid); Polyester-7 (copolymer of trimethylolpropane, Adipic Acid, Neopentyl Glycol and Hexanediol); Polyester-8 (copolymer of adipic acid and neopentyl glycol end-capped with octyldodecanol or a cyanodiphenylpropenoyl group); Polyester-10 (thermal condensation product of hexanediol, neopentyl glycol and adipic acid and pyromellitic dianhydride); Polyester-10; Polyester-11; Polyester-12; Polyester-13 (copolymer of diethylene glycol, 1,4-cyclohexanedimethanol, trimethylolpropane, and the simple esters of 1,4-cyclohexanedicarboxylic acid and sulfoisophthalic acid); Polyester-14 (copolymer of propylene glycol, terephthalic acid, dimethyl terephthalate, Steareth-50, ethylene glycol and pentaerythritol); Polyester-15; Polyester-16 (sodium salt of a copolymer of dimethyl sodiosulfosiophthalic acid, dimethyl terephthalate, ethylene glycol and isophtalic acid monomers); Polyester-16 ; Polyester-17; Polyester-18 (condensation of fumaric acid, methylhexahydrophthalic aicd, dimethyl propanediol, and cyclohexane dimethanol); Polyester-19 (reaction of octyldodecanol, dimer dilinoleyl alcohol, succinic acid and *Argania spinosa* kernel oil; Polyester-21 (octyldodecanol, dimer dilinoleyl alcohol, succinic acid, and *Punica granatum* seed oil); Polyester-22 (reaction product of octyldodecanol, dimer dilinoleyl alcohol, succinic acid, and *Vaccinium myrtillus* seed oil); and so on.

If desired, the pigment complex may contain, in addition to the carbon black and/or the polyester or polyamide, one or more film forming polymers, preferably those derived from ethylenically unsaturated monomers, for example, PVP; acrylic acid, methacrylic acid or their simple $C_{1-20}$ alkyl esters and so on.

It may also be desirable for the pigment complex to contain one or more non-ionic organic surfactants especially in the form of alkoxylated alcohols, more specifically alkoxylated fatty alcohols such as Laureth, Steareth, Ceteth, Ceteareth, Beheneth, Isosteareth, with the number of repeating oxyethylene units ranging from 2 to 300.

In one most preferred embodiment the pigment complex is comprised of the pigment, preferably carbon black; at least one polyester or polyamide; at least one film forming polymer; and at least one organic non-ionic surfactant. More specifically, the pigment complex comprises from 1-80 parts pigment (such as carbon black); from 1-50 parts polyester or polyamide (e.g. Polyester-5); from 1-40 parts film forming polymer (e.g. PVP); and from 1-20 parts nonionic organic surfactant (Laureth-4). Most preferred is a pigment complex comprising 40 parts Black 2 (carbon black); 31 parts Polyester-5; 24 parts PVP; and 4.5 parts Laureth-4.

The preferred pigment composition comprises the organic pigments and pigment complex in ratios ranging from about 1 part organic pigment to 1 part pigment complex to 1 part organic pigment to 20 parts pigment complex by weight. In another more preferred embodiment the pigment composition comprises only the carbon black and the organic pigment, preferably D&C blue and they are present in a ratio ranging from 1 part organic pigment to 1 part carbon black to 1 part organic pigment to 20 parts carbon black. Such pigment composition may have a contrast ratio ranging from 35 to 80.

In the most preferred embodiment of the invention the pigment composition comprises from about about 1 part of D&C blue and 2 to 5 parts of a pigment complex comprised of carbon black/Polyester-5/PVP/Laureth-4 (40:31:24.5:4.5) with the total pigment composition being 1 to 20% of the total cosmetic composition.

Other Ingredients

The cosmetic composition of the invention may contain additional ingredients, provided that they do not affect the desired pigment contrast ratio ranging from 35 to 80. Examples of such additional ingredients include preservatives, other film forming polymers, emollients, conditioning agents, and the like.

The invention will be further described in connection with the following Examples which are set forth for the purposes of illustration only.

EXAMPLE 1

| Ingredient | % by weight | |
|---|---|---|
| Dimethicone silylate/isododecane (40:60) (DC 7-4405 Cosmetic Fluid) | 75.00 | 80.25 |
| Dimethicone gum (GE Silicones SE-30) | | 10.00 |
| Trimethylsiloxysilicate | | 5.00 |
| Hydrogenated styrene/isoprene copolymer | 20 | |
| Black 2/polyester-5/PVP/Laureth-4 (40:31:24.5:4.5) | 2.50 | 3.50 |
| Isododecane | 1.50 | |
| FD&C Blue No. 1 Aluminum Lake | 0.50 | 0.75 |
| Caprylyl glycol/phenoxyethanol/hexylene glycol (55:35:10) | 0.30 | 0.30 |
| Panthenol | 0.10 | 0.10 |
| Panthenyl ethyl ether | 0.10 | 0.10 |

EXAMPLE 2

Compositions were prepared as follows:

| Ingredient | % by weight | | | | | | | | | |
|---|---|---|---|---|---|---|---|---|---|---|
| | 1 | 2 | 3 | 4 | 5 | 6 | 7 | 8 | 9 | 10 |
| Progel II[1] | 30.6 | | | | | | | | | |
| Gel ID[2] | 27.8 | 25.15 | 21.15 | 20.15 | 20.15 | 10.00 | | | | |
| DC7-4405[3] | 17.43 | 70.00 | 70.00 | 70.00 | 70.00 | | | 75.25 | 80.25 | 80.25 |
| Isododecane | 15.8 | | | | | 45.25 | | | | |
| Dimethicone (1.5cs) | | | | | | | 55.25 | | | 5.00 |
| Dimethicone (gum) | | | | | | | 10.00 | 15.00 | 10.00 | 5.00 |
| Trimethylsiloxysilicate | | | | 5.00 | | 30.00 | 30.00 | 5.00 | 5.00 | 5.00 |
| Polymethylsilsesquioxane | | | | | | 10.00 | | | | |

-continued

| Ingredient | % by weight | | | | | | | | | |
|---|---|---|---|---|---|---|---|---|---|---|
| | 1 | 2 | 3 | 4 | 5 | 6 | 7 | 8 | 9 | 10 |
| MQ-1640[4] | | | | | 5.00 | | | | | |
| Gransil MMT Fluid[5] | | 2.00 | | | | | | | | |
| Gransil PMT Fluid[6] | | 2.00 | | | | | | | | |
| Ethanol | 4.37 | | | | | | | | | |
| Black iron Oxide | 3.20 | | | | | | | | | |
| FD&C Blue No. 1 | 0.46 | | | | | | | | | |
| Blue[7] | | | 1.00 | 1.00 | 1.00 | 0.75 | 0.75 | 0.75 | | 0.75 |
| PreserVative[8] | 0.28 | 0.30 | 0.30 | 0.30 | 0.30 | 0.30 | 0.30 | 0.30 | 0.30 | 0.30 |
| PanThenol | | 0.10 | 0.10 | 0.10 | 0.10 | 0.10 | 0.10 | 0.10 | 0.10 | 0.10 |
| Ethyl Panthenol | 0.06 | 0.10 | 0.10 | 0.10 | 0.10 | 0.10 | 0.10 | 0.10 | 0.10 | 0.10 |
| Black Chip[9] | | 3.35 | 3.35 | 3.35 | 3.35 | 3.50 | 3.50 | 3.50 | 3.50 | 3.50 |

[1]Hydrogenated styrene/isoprene copolymer/isododecane (10:90)
[2]Propylene carbonate/isododecane/quaternium-90 bentonite (2.5:80:17.5)
[3]Dimethicone silylate/isododecane (40:60)
[4]Trimethylsiloxysilicate/polypropylsilsesquioxane (60:40)
[5]Dimethicone/mercaptopropyl methicone copolymer
[6]Dimethicone/mercaptopropyl methicone copolymer/phenyl trimethicone (37.5:62.5)
[7]FD&C Blue No. 1/Aluminum Lake/triethoxycaprylylsilane (99:1)
[8]Caprylyl glycol/phenoxyethanol/hexylene glycol (55:35:10)
[9]Black 2/Polyester-5/PVP/Laureth-4 (40:31:24.5:4.5)

EXAMPLE 3

The compositions in Example 2 were comparatively tested for properties that contribute to commercial acceptability, in particular, smudging, tackiness, dry time, wear, and resistance to wash off.

Smudge/Flake Tests

On False Eyelashes

Smudge/Flake on False Eyelashes: The composition was applied to 2 brown false eyelashes using a flocked applicator and allowed to dry on the lashes for 1 day. One of the lashes was washed and the other was left untouched. Using cream cleanser and water, one set of lashes was rubbed between the fingers. If the composition came off in the form of black flakes, flaking was noted. If the composition came off on the fingers as dissolved into the white cream cleanser and making it look gray it was noted as smudging. A paper towel was used to dab the lashes dry and any composition transfer to the towel was noted as transfer. A total of 3 washings were performed on the test lashes.

On Human Lashes

The compositions were applied to human lashes using a flocked applicator. The composition was allowed to dry for at least 5 hours. The lashes were washed with a cream cleanser and water, then rinsed with water. The lashes were dabbed with a paper towel. If the composition smudged onto the towel, smudge was noted. If the product flaked off the lashes it was noted as flaking On Plate The composition was drawn down onto a porcelain plate and left to dry for one day. One drop of water was placed on the top of the dried down film. Using a finger the drop of water was rubbed 10 times off and on the drawn down film to see if the film smudged or flaked. The white portion of the plate was checked to see if any composition transferred. Then one drop of oil was placed on top of the drawn down film. Using a finger the oil droplet was rubbed ten times on and off the drawn down film to see if the formula smudged or flaked. The white part of the plate was checked to see if anything transferred. On the dry part of the draw down a finger was used to rub the formula onto a clean part of the plate to see if any smudging or flaking occurred. Any smudging or flaking was noted.

Tack Assessment:

Dry time was performed only on compositions applied to human lashes. When the eye naturally blinked if the formula transferred from the top lash to the bottom of the eye it was noted as poor dry time. If the top lash stuck to the bottom lash it was noted as tacky.

The results are as follows:

| | % by weight | | | | | | | | | |
|---|---|---|---|---|---|---|---|---|---|---|
| | 1 | 2 | 3 | 4 | 5 | 6 | 7 | 8 | 9 | 10 |
| Smudge On False Lashes | Yes | No | No transfer | No | No | Flake | No | No | No | No |
| Smudge on Eyes | Blue | | | | | | | No | No | No |

-continued

| | % by weight | | | | | | | | | |
|---|---|---|---|---|---|---|---|---|---|---|
| | 1 | 2 | 3 | 4 | 5 | 6 | 7 | 8 | 9 | 10 |
| Smudge on Plate | Yes | No | Yes | No transfer | No transfer | Flake | No | No | No | No |
| Tack | Slight | | | Slight | | | | No | No | No |
| Dry Time | Good | | | Good | | | | Good | Good | Good |
| 1 wash | Blue, bled, some black left on lashes | No transfer | No transfer | No transfer | No transfer | Flake | No transfer | No transfer | No transfer | No transfer |
| 2 wash | Blue, bled, some black left on lashes | No transfer | No transfer | No transfer | No transfer | Flake | No transfer | No transfer | No transfer | No transfer |
| 3 wash | Blue bled, some black | No transfer | No transfer | No transfer | No transfer | Flake | No transfer | No transfer | No transfer | No transfer |

EXAMPLE 4

The following compositions were prepared:

| | % by weight | |
|---|---|---|
| Ingredient | Formula A | Formula B |
| Dow Corning 7-4411 cosmetic fluid | 65.25 | 66.00 |
| Dimethicone (GE SE-30) | 10.00 | 10.00 |
| Trimethylsiloxysilicate | 10.00 | 10.00 |
| Dimethicone 1.5 cst | 10.00 | |
| D&C Black #2/polyethylene | 3.50 | 3.50 |
| FD&C Blue No. 1 Aluminum Lake/triethoxycaprylylsilane | 0.75 | — |
| Caprylyl glycol/phenoxyethanol/hexylene glycol | 0.30 | 0.30 |
| Panthenol | 0.10 | 0.10 |
| Panthenyl ethyl ether | 0.10 | 0.10 |

The compositions were prepared by combining the ingredients and mixing well.

EXAMPLE 5

Compositions A and B were tested for opacity by drawing samples down on a black and white Lenetta card. Each sample was drawn down using a draw down bar to a thickness of 3 mil (thousandths of an inch). Three separate draw downs were made for each sample. The draw downs were placed into a 50° C. oven until dry to the touch. "Dry to the touch" is determined by placing a finger on the sample and ascertaining dryness. Each sample card was read using a Gretag Macbeth Color iControl spectrophotometer using the Opacity CR setting. For each card, the Gretag Macbeth ColorEye XTH sensor was placed on top of the area of the card having the white background. Three opacity readings were taken. The ColorEye XTH sensor was then placed on the area of the card containing the draw down. Three more opacity readings were taken. The process was repeated with each draw down card. The ratio between the average of the readings on the white portion of the card and the average of the readings taken on the sample draw down is the contrast ratio. The pigment contrast ratio for Sample A was 49.08 and the pigment contrast ratio for Sample B was 29.14. The data illustrates that the composition of the invention exhibits a substantially improved pigment contrast ratio which in turn results in more intense color.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A cosmetic composition comprising at least one volatile solvent selected from the group consisting of isododecane, isohexadecane, hexamethyl disiloxane, octamethyl trisiloxane, decamethyltetrasiloxane, dodecamethylpentasiloxane, and mixtures thereof, at least one crosslinked silicone film former, which is selected from the group consisting of trimethyl siloxysilicate, dimethicone silylate and mixtures thereof, at least one silicone gum, and at least one pigment complex comprised of carbon black; a polyester selected from the group consisting of Polyester-1, 2, 3, 4, 5, 6, 7, 8, 9, 10, 11, 12 and mixtures thereof; a film forming polymer that is PVP; and a non-ionic organic surfactant that is an alkoxylated fatty alcohol having from 2-300 repeating oxyethylene units and at least one D&C or FD&C blue pigment or Lake thereof in a ratio of 1 to 20 parts pigment complex to 1 part D&C or FD&C blue pigment or Lake thereof.

2. The cosmetic composition of claim 1 wherein the pigment complex and the at least one D&C or FD&C color are the only pigments present in the composition.

3. The cosmetic composition of claim 1 wherein the polyester is polyester 5.

4. The cosmetic composition of claim 1 wherein the pigment complex comprises carbon black, Polyester-5, PVP, and Laureth-4.

5. The cosmetic composition of claim 4 wherein the pigment complex comprises 1-80 parts carbon black; from 1-50 parts Polyester-5; from 1-40 parts PVP; and from 1-20 parts Laureth-4.

6. The cosmetic composition of claim 1 wherein the volatile solvent is isododecane.

7. The cosmetic composition of claim 1 wherein the volatile solvent comprises a mixture of isododecane and one or more silicones selected from hexamethyldisiloxane, octamethyltrisiloxane, or decamethyltetrasiloxane.

8. The cosmetic composition of claim 1 wherein the crosslinked silicone film former is a a mixture of trimethyl siloxysilicate and dimethicone silylate.

9. The composition of claim 1 wherein the crosslinked silicone film former is trimethylsiloxysilicate.

* * * * *